(12) United States Patent
Storr et al.

(10) Patent No.: US 11,478,757 B2
(45) Date of Patent: Oct. 25, 2022

(54) HIGH CUT-OFF HEMODIALYSIS MEMBRANE FOR USE IN LIVER DIALYSIS

(75) Inventors: Markus Storr, Filderstadt (DE); Bernd Krause, Rangendingen (DE); Hermann Goehl, Bisingen (DE); Thomas Ertl, Bisingen (DE); Alexander Gekeler, Pfullingen (DE)

(73) Assignee: GAMBRO LUNDIA AB, Lund (SE)

( * ) Notice: Subject to any disclaimer, the term of this patent is extended or adjusted under 35 U.S.C. 154(b) by 1473 days.

(21) Appl. No.: 13/578,161

(22) PCT Filed: Apr. 13, 2011

(86) PCT No.: PCT/EP2011/055798
§ 371 (c)(1),
(2), (4) Date: Aug. 9, 2012

(87) PCT Pub. No.: WO2011/131534
PCT Pub. Date: Oct. 27, 2011

(65) Prior Publication Data
US 2012/0305486 A1    Dec. 6, 2012

(30) Foreign Application Priority Data
Apr. 20, 2010 (EP) .................................. 10160453

(51) Int. Cl.
*B01D 69/08* (2006.01)
*A61M 1/16* (2006.01)
(Continued)

(52) U.S. Cl.
CPC .......... *B01D 67/0009* (2013.01); *A61M 1/16* (2013.01); *A61M 1/1696* (2013.01); *B01D 69/08* (2013.01);
(Continued)

(58) Field of Classification Search
CPC ............ A61M 1/16; A61M 1/34; B01D 67/00
See application file for complete search history.

(56) References Cited

U.S. PATENT DOCUMENTS 5,744,042 A * 4/1998 Stange ................ A61M 1/1654
210/644
2004/0217055 A1 * 11/2004 Kraus .................... A61K 38/38
210/645

(Continued)

FOREIGN PATENT DOCUMENTS

| EP | 0615780 | 9/1994 |
|---|---|---|
| EP | 1388364 | 2/2004 |
| WO | WO2004/056460 | 7/2004 |

OTHER PUBLICATIONS

Cecie Starr et al., Biology: Concepts and Applications 562 (7th ed. 2008).*

(Continued)

*Primary Examiner* — Magali P Slawski
*Assistant Examiner* — Brad Gordon
(74) *Attorney, Agent, or Firm* — Barnes & Thornburg LLP (57) ABSTRACT

A system for liver dialysis makes use of a high cut-off hemodialysis membrane for removing water-soluble and protein-bound toxins from the blood of a person in need. A high cut-off hollow fiber hemodialysis membrane has improved potential to remove albumin-bound toxins and inflammatory mediators.

12 Claims, 8 Drawing Sheets

(51) Int. Cl.
*B01D 67/00* (2006.01)
*B01D 71/68* (2006.01)

(52) U.S. Cl.
CPC ........... *B01D 69/087* (2013.01); *B01D 71/68* (2013.01); *A61M 2210/1071* (2013.01); *B01D 2325/20* (2013.01)

(56) References Cited

U.S. PATENT DOCUMENTS

| | | | | |
|---|---|---|---|---|
| 2005/0115898 | A1* | 6/2005 | Sternby | A61M 1/16 210/636 |
| 2006/0129082 | A1* | 6/2006 | Rozga | A61M 1/3472 604/6.04 |
| 2006/0144782 | A1* | 7/2006 | Buck | B01D 67/0002 210/500.23 |
| 2006/0186044 | A1* | 8/2006 | Nalesso | A61M 1/3472 210/645 |
| 2007/0181499 | A1* | 8/2007 | Roberts | A61M 1/3472 210/645 |

OTHER PUBLICATIONS

Arthur E. Baue et al., Multiple Organ Failure: Pathophysiology, Prevention, and Therapy 48 (2000).*
Nancy Rolando et al., The Systematic Inflammatory Response Syndrome in Acute Liver Failure 32 Hepatology 734, 734-739 (2000).*
Giancarlo Liumbruno et al., Recommendations for the use of albumin and immunoglobins, 7 Blood Transfus, 216, 216, (2009).*
Lee C. Vermeulen, Jr. et al., A Paradigm for Consensus: The University Hospital Consortium Guidelines for the Use of Albumin, Nonprotein Colloid, and Crystalloid Solutions, 155 Arch. Intern. Med. 373, 377 (1995).*
Christopher D. Hillyer et al., Blood Banking and Transfusion Medicine: Basic Principles & Practice 281 (2d ed. 2007).*
Stadlbauer et al., Removal of Bile Acids by Two Different Extracorporeal Liver Support Systems in Acute-on-Chronic Liver Failure, 53 Asaio Journal 187, 187-193 (2007).*
Peszynski et al., Albumin dialysis: single pass vs. recirculation (MARS), 22 Liver 40, 41 (2002).*
Wang et al., Effect of hemoperfusion cartridge on different internal environmental indicators, 4 World J. Emerg. Med. 290, 292 (2013).*
Gambro, MARS Newsletter 1 (2008).*
Stadlbauer et al., Removal of Bile Acids by Two Different Extracorporeal Liver Support Systems in Acute-on-Chronic Liver Failure, 53 Asaio Journal 187, 187-193 (2007). (Year: 2007).*
Peszynski et al., Albumin dialysis: single pass vs. recirculation (MARS), 22 Liver 40, 41 (2002). (Year: 2002).*
Wang et al., Effect of hemoperfusion cartridge on different internal environmental indicators, 4 World J. Emerg. Med. 290, 292 (2013). (Year: 2013).*
Gambro, MARS Newsletter 1 (2008). (Year: 2008).*
Leypoldt, J. K., et al., "Dextran Sieving Coefficients of Hemofiltration Membranes", 1983, Trans. Am. Soc. Artif. Intern. Organs, vol. 29, pp. 678-683.
"Hamodialysatoren, Hamodiafilter, Hamofilter, Hamokonzentratoren und Dazugehorige Blutschlauchsysteme", Apr. 1996, European Standard, European Committee for Standardization, EN1283.
Morgera, Stanislao, et al., "Intermittent High Permeability Hemofiltration in Septic Patients with Acute Renal Failure", 2003, Intensive Care Med., No. 29, pp. 1989-1995.
Cardiovascular Implants and Artificial Organs—Haemodialysers, Haemodiafilters, Haemofilters, and Haemoconcentrators, Oct. 2004, International Standard; ISO 8637.
Ward, Richard A., et al., "Protein-Leaking Membranes for Hemodialysis: A New Class of Membranes in Search of an Application", 2005, Journal American Society of Nephrology, No. 16, pp. 2421-2430.
PCT International Search Report and Written Opinion for PCT/EP2011/055798, dated May 30, 2011.

* cited by examiner

HIGH CUT-OFF HEMODIALYSIS MEMBRANE FOR USE IN LIVER DIALYSIS

CROSS REFERENCE TO RELATED APPLICATIONS

This application is the U.S. national phase of PCT/EP2011/055798 filed Apr. 13, 2011. PCT/EP2011/055798 claims the benefit under the Convention of the Apr. 20, 2010 filing date of EP 10160453.6. PCT/EP2011/055798 and EP 10160453.6 are hereby incorporated herein by reference.

TECHNICAL FIELD

The present disclosure relates to an improved system for liver dialysis, which makes use of a high cut-off hemodialysis membrane for removing water-soluble and protein bound toxins from the blood of a person in need. The specific hollow fiber membrane has the potential to improve the removal of albumin bound toxins and of inflammatory mediators. The present disclosure also relates to a high cut-off hemodialysis membrane for the treatment of liver failure.

DESCRIPTION OF THE RELATED ART

Liver dialysis is a detoxification treatment for liver failure and is used for patients with various liver disorders, such as, for example, hepatorenal syndrome, decompensated chronic liver disease, acute liver failure, graft dysfunction after liver transplantation, liver failure after liver surgery, secondary liver failure, multi organ failure or intractable pruritus in cholestasis. It is similar to hemodialysis and based on the same principles. Like a bioartificial liver device, it is a form of artificial extracorporeal liver support.

The so-called hepatorenal syndrome (HRS) is a life-threatening medical condition that consists of rapid deterioration in kidney function in individuals with cirrhosis or massive liver failure. HRS is usually fatal unless a liver transplant is performed, although various treatments, such as dialysis, can prevent advancement of the condition.

HRS can affect individuals with cirrhosis (regardless of cause), severe alcoholic hepatitis, or massive hepatic failure, and usually occurs when liver function deteriorates rapidly because of an acute injury such as an infection, bleeding in the gastrointestinal tract, or overuse of diuretic medications. HRS is a relatively common complication of cirrhosis, occurring in 18% of cirrhotics within one year of their diagnosis, and in 39% of cirrhotics within five years of their diagnosis. Deteriorating liver function is believed to cause changes in the circulation that supplies the intestines, altering blood flow and blood vessel tone in the kidneys. The renal failure of HRS is a consequence of these changes in blood flow, rather than direct damage to the kidney. Two forms of hepatorenal syndrome have been defined: Type 1 HRS entails a rapidly progressive decline in kidney function, while type 2 HRS is associated with ascites (fluid accumulation in the abdomen) that does not improve with standard diuretic medications.

For example, the risk of death in hepatorenal syndrome is very high; the mortality of individuals with type 1 HRS is over 50% over the short term. The only long-term treatment option for the condition is liver transplantation. As a short-term treatment option before transplantation, liver dialysis may turn out to be vitally important for the patient.

A critical issue of the clinical syndrome in liver failure is the accumulation of toxins not cleared by the failing liver. Based on this hypothesis, the removal of lipophilic, albumin-bound substances such as bilirubin, bile acids, metabolites of aromatic amino acids, medium-chain fatty acids and cytokines should be beneficial to the clinical course of a patient in liver failure.

Figure 1:
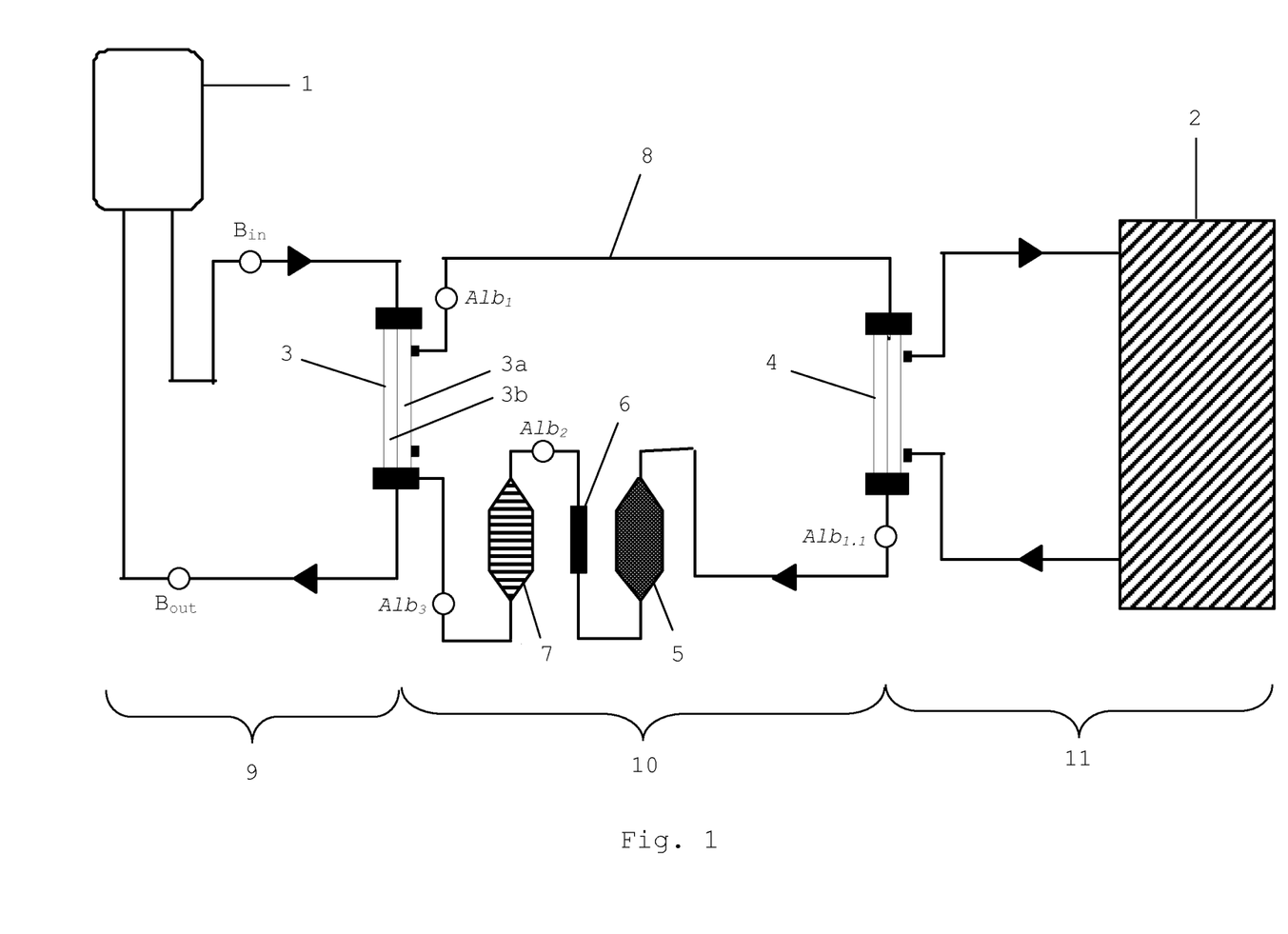

In liver dialysis systems, such as the Molecular Adsorbent Recycling System (MARS®) blood is cleansed in an extracorporeal circuit that is a combination of both kidney and liver dialysis (FIG. 1). Established methods for kidney dialysis alone are not applicable for liver failure because kidney dialysis removes water-soluble toxins only. The liver normally removes albumin bound toxins. Albumin is a protein found in the blood that carries water insoluble substances including toxins. For this reason, systems like the MARS® system make use of human albumin to cleanse the blood because the albumin removes the toxins which are bound to albumin in the blood that the aqueous solution in kidney dialysis cannot remove, such as unconjugated bilirubin, bile acids, hydrophobic amino and fatty acids. A significant portion of toxins are water-soluble molecules of low- and middle-molecular weight, the concentration of which may be increased by hepatic failure and renal failure. These molecules can effectively be removed by hemodialysis. The MARS® system is thus thought to replace the detoxification function of the liver with regard to water-soluble and albumin-bound toxins. The principles of this system are already described in EP 0 615 780 A1.

As shown in FIG. 1, the patient's (1) blood is passed into a hollow fiber membrane hemodialyzer. The dialysate side of the dialyzer (3a) provides for clean human albumin that acts as a dialysate. As the patient's blood moves along the membrane, water-soluble and protein bound toxins in the blood are transported through the membrane and into the dialysate albumin solution on the other side (8). The membrane is impermeable to albumin and to other valuable proteins such as hormones and clotting factors, keeping them in the patient's circulation. The cleansed blood then returns to the patient. Meanwhile, the albumin solution carrying the toxins is recycled by passing first through a low-flux dialyzer (4) opposite of a buffered aqueous solution. This process is similar to that found in kidney dialysis and removes water-soluble substances from the albumin solution. The albumin then passes through an activated carbon adsorber (5) and, after passing a filter which removes carbon particles (6), passes through an anion exchanger (7) that removes toxins bound to albumin. The recycled albumin can then again enter the dialyzer (3) and bind again to toxins which can thus be removed from the patient's blood.

Another liver dialysis system is the so called Single Pass Albumin Dialysis (SPAD), which is a simple method of albumin dialysis using standard renal replacement therapy machines without an additional perfusion pump system. The patient's blood flows through a circuit with a high-flux hollow fiber hemodialyzer, comparable to that used in the conventional MARS® system. The other side of this membrane is also cleansed with an albumin solution in counter-directional flow, which is, however, discarded after passing the filter.

Conventionally, liver dialysis systems like the ones described comprise a high-flux dialyzer membrane with a molecular weight cut-off of 15 to 20 kDa in the presence of whole blood. For example, the MARS® system makes use of a high-flux membrane (3) (FIG. 1) which is a blend of polyethersulfone, polyvinyl pyrrolidone and polyamide (MARS®Flux).

The Prometheus system utilizes a so-called AlbuFlow® membrane, which is permeable for larger proteins such as albumin, clotting factors and immunoglobulins. The system does not require exogenous albumin in the secondary circuit since endogenous albumin enters the secondary circuit via the AlbuFlow® membrane. The drawback of the system is that clotting factors which may enter the secondary circuit are eliminated, resulting in potential coagulation problems during treatment sessions.

The Arbios system applies an ultrafiltration treatment via the Sepet™ membrane which is, however, associated with a loss of albumin and larger proteins. Therefore, the system requires substantial substitution with albumin solution or with fresh frozen plasma.

The current systems which are based on high-flux dialyzers, such as the MARS® system, on the other hand, have limitations with regard their elimination performance concerning strongly bound toxins, such as unconjugated bilirubin. Due to the pore size and more specifically the pore diameter of high-flux membranes (12 nm and 9 nm) there is only limited transmembrane elimination of inflammatory mediators (e.g. cytokines) achievable with the current systems such as the MARS® system.

In order to improve efficiency with regard to removal of certain molecules, a new class of membranes that leak proteins below defined molecular weight cut offs (further referred to as "protein-leaking" membranes) have been developed for hemodialysis more recently. These membranes provide greater clearances of low molecular weight proteins and small protein-bound solutes that conventional high-flux dialysis membranes will not remove. However, this goes at the cost of some albumin loss into the dialysate. While in a small number of clinical trials some improvements could be achieved using protein-leaking membranes, it remains unclear yet that routine use of protein-leaking membranes is warranted. It is also unclear whether protein-leaking membranes offer benefits beyond those obtained with conventional high-flux membranes, when the latter are used in convective therapies, such as hemofiltration and hemodiafiltration. Finally, the amount of albumin loss that can be tolerated by hemodialysis patients in a long-term therapy has yet to be determined (Ward, R. A., J. Am. Soc. Nephrol. 16, 2005, 2421-2430).

WO 2004/056460 discloses High cut-off (HCO) membranes which can be used in dialyzers to eliminate circulating sepsis-associated inflammatory mediators more effectively than using conventional dialysis membranes. These High Cut-off membranes have much higher pore size than the above mentioned types. Pore sizes (diameter) are in the range of 20 to 40 nm, three times larger than conventional (slightly) protein-leaking membranes and by a factor of four larger than the standard high-flux membranes (12 nm and 9 nm, respectively). The High Cut-off membranes have a molecular weight cut-off, measured in the presence of whole blood, of 45 kDa whereas the cut-off of the other types of membranes usually does not exceed 20 kDa (see also above). This cut-off as measured in blood clearly indicates that substances, like smaller proteins, with a molecular weight from 20 to 45 kDa can penetrate these High Cut-off membranes to a significant degree. However, hemodialysis with High Cut-off membrane dialyzers alone is not capable of eliminating protein bound toxins.

The applicants have now found that such High Cut-off membranes can be used to effectively treat patients suffering from liver failure. The membranes can replace the standard high-flux membranes which are currently used in the above-described liver support systems.

The High Cut-off membrane when used instead of the conventional high-flux membranes, e.g. in the MARS system, results in a significant improvement in the detoxification efficiency of the system. In particular, strongly albumin bound liver toxins, such as unconjugated bilirubin, are eliminated at a markedly increased rate. Furthermore, the relatively large pores of the High Cut-off membrane facilitate the elimination of inflammatory cytokines such as interleukin 1β (IL-1β) or interleukin 6 (IL-6). The accumulation of pro-inflammatory cytokines in acute liver failure is associated with a high mortality. IL-6, IL-1β and TNF are known to induce massive necrotic inflammation of liver tissue.

The invention thus provides an improved extracorporeal liver support system for the treatment of liver failure which overcomes the drawbacks of the prior art systems.

SUMMARY

It is an object of the present invention to provide an improved liver support system wherein the conventionally used high-flux dialyzers are replaced by High Cut-off membrane dialyzers in order to better remove strongly albumin-bound liver toxins. The present invention thus relates to a liver support system which comprises a High Cut-off membrane for removing protein-bound toxins and inflammatory cytokines. The expression "High Cut-off membrane", in the context of the present invention, refers to membranes which are characterized by allowing the passage of molecules having a molecular weight of up to 45 kDa in presence of whole blood, and with a molecular weight exclusion limit in water of about 200 kDa. The High Cut-off membrane may further be characterized by a pore size of from 20 to 40 nm.

According to one aspect of the invention, the liver support system makes use of the High Cut-off membrane for eliminating protein-bound toxins and inflammatory cytokines from the blood of a patient.

According to one aspect, the invention relates to a liver support system comprising a High Cut-off membrane for eliminating protein-bound toxins and inflammatory cytokines from the blood of a patient, wherein the albumin concentration in the dialysis fluid is in the range of 1% to 25% by weight, preferably in the range of 2.0% to 20% by weight.

According to a further aspect, the invention relates to a dialysis membrane for the treatment of liver failure, wherein the membrane has a pore size of from 20 to 40 nm and allows the passage of molecules having a molecular weight of up to 45 kDa in presence of whole blood, and with a molecular weight exclusion limit in water of about 200 kDa.

According to yet a further aspect, the invention relates to a hemodialysis device for conducting liver dialysis on a patient suffering from liver failure, comprising a dialysis membrane that allows the passage of molecules having a molecular weight of up to 45 kDa in presence of whole blood, and with a molecular weight exclusion limit in water of about 200 kDa.

BRIEF DESCRIPTION OF THE DRAWINGS

FIG. 1 shows the setup of a liver support system according to the invention. The patient's (1) blood is passed into a hollow fiber membrane dialyzer (3b). The dialysate side of the dialyzer (3a) provides for a dialysate solution comprising clean human albumin. Water-soluble and protein bound toxins in the blood are transported through the membrane and into the dialysate albumin solution on the other side (8). The cleansed blood returns to the patient. This part of the system (9) can be referred to as the "blood circuit". The albumin solution carrying the toxins is recycled by passing first through a low-flux dialyzer (4) opposite of a buffered aqueous solution (the "dialysate circuit" (11)). The albumin then passes through an activated carbon adsorber (5) and, after passing a filter which removes carbon particles (6), passes through an anion exchanger (7) that removes toxins bound to albumin. This part of the system may be referred to as the "albumin circuit" (10). The recycled albumin can then again enter the dialyzer (3). The dialysis machine used within the system is displayed as (2). Circles (○) denote where test samples for analysis are taken.

FIG. 5 A depicts the development of the bilirubin concentration in the blood circuit with a HSA concentration in the albumin circuit of 10% at 0 min. FIG. 5 B depicts the development of the bilirubin concentration in the blood circuit with a HSA concentration in the albumin circuit of 5% at 0 min.

FIG. 6 A depicts the development of the bile acid concentration in the blood circuit with a HSA concentration in the albumin circuit of 10% at 0 min. FIG. 6 B depicts the development of the bile acid concentration in the blood circuit with a HSA concentration in the albumin circuit of 5% at 0 min.

DETAILED DESCRIPTION

Figure 2:
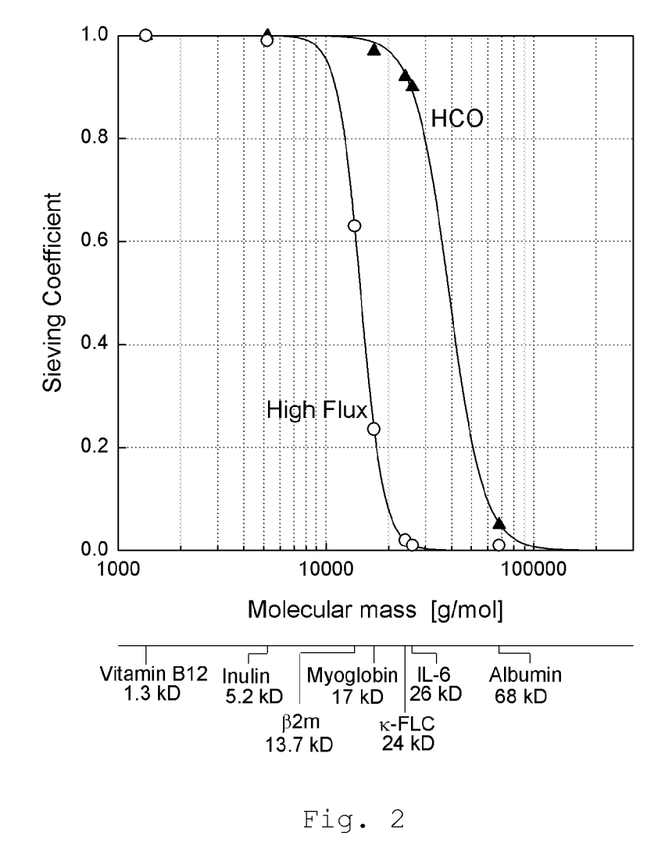
FIG. 2 shows the sieving coefficients of a high-flux dialysis membrane and a High Cut-off dialysis membrane. The sieving coefficients shown have been derived from clinical studies. Dialysis has been performed according to the method described in Morgera et al. (2003): Intermittent high permeability haemofiltration in septic patients with acute renal failure. Intensive Care Med. 29, 1989-1995. The HCO 1100® dialyzer (Gambro Lundia AB) serves as an example for a High Cut-Off dialysis membrane. The conventional high-flux dialyzer used is Polyflux® 170H (Gambro Lundia AB).

Liver dialysis according to the invention is preferably carried out using a dialyzer comprising a High Cut-off dialysis membrane (3) which allows passage of molecules having a molecular weight of up to 45 kDa in the presence of whole blood and have a molecular weight exclusion limit in water of about 200 kDa. As can be seen from FIG. 2, the High Cut-off dialysis membrane allows the limited passage, in whole blood, of molecules up to 70 kD, including albumin with a molecular weight of 68 kD. The molecular weight cut-off (MWCO) of the High Cut-off dialysis membrane is higher than the MWCO of the conventional high-flux membrane (FIG. 2), which generally lies in the range of 15 to 20 kDa. FIG. 2 demonstrates that the high-flux membrane as used allows the passage of molecules up to 25 kD only.

Liver dialysis according to the invention is carried out (FIG. 1) by passing the patient's (1) blood into the High Cut-off membrane dialyzer (3). The dialysate side of the dialyzer (3a) provides for clean human serum albumin (HSA) that acts as a dialysate. The concentration of the HSA may vary. In general, it may be in the range of 1% to 25% by weight. A range of 2% to 20% by weight of HSA is preferable. A range of 5% to 20% by weight of HSA is used with special preference. Liver dialysis systems like the MARS® system are preferably run with a HSA concentration of 10%-25%. HSA concentration may lie in the range of from 5% to 12%, however, if a system according to the invention is used. Systems like SPAD are preferably run with a HSA concentration of 2%-5%. The HSA solution may further contain a physiological amount of NaCl, e.g. 0.9% NaCl. Water-soluble and protein bound toxins in the blood (3b) are transported through the membrane and into the dialysate albumin solution on the other side (3a), which marks the passage into the albumin circuit (10). The cleansed blood returns to the patient.

The albumin solution in the HSA circuit carrying the toxins is recycled by passing first through a standard low-flux dialyzer (4) opposite of a buffered aqueous solution in order to remove water-soluble substances from the albumin. An example for such low-flux dialyzer is the diaFLUX 1.8 dialyzer used in the MARS® system.

Afterwards, the albumin passes through an activated carbon adsorber (5). For example, the MARS® system uses vapor-activated carbon, which is used to clean the HSA dialysate in the HSA circuit (diaMARS® AC250). The carbon is especially suited for removing low-molecular, non-polar compounds. After passing a filter for removing carbon particles (6), the HSA dialysate passes through an anion exchanger (7) that especially removes anionic molecules, such as bilirubin (diaMARS® IE250). Inflammatory molecules such as cytokines are also removed in the HSA circuit and will not re-enter the blood circuit. The recycled albumin then re-enters the dialyzer (3) and binds again to toxins which can thus be removed from the patient's blood.

Flow rates used in the liver dialysis system may vary. It is advantageous to use flow rates with a $Q_B$ (blood flow) of 100-500 ml/min, preferably 150-250 ml/min, a $Q_{Alb}$ (flow in the albumin circuit) of 100-500 ml/min, preferably 150-250 ml/min and a $Q_D$ (dialysate circuit) of 10-1000 ml/min, preferably 50-500 ml/min.

Typically, the High Cut-off membranes according to the invention have a water permeability of >40 ml/h per mmHg/m² in vitro. They may have a $\beta_2$-microglobulin clearance of at least 80 ml/min for conventional hemodialysis with a blood flow rate of 300 to 400 ml/min. Albumin loss is preferably 0.5 to 2 g, in particular 1.0 to 1.5 g per hour of dialysis. The sieving coefficient may be 0.9 to 1.0 for $\beta_2$-microglobulin and 0.01 to 0.1, preferably 0.03 to 0.07, for albumin, when measured according to EN 1283. Measured in the presence of whole blood, the sieving coefficient is preferably smaller than 0.05, in particular smaller than 0.01 (see Table I).

TABLE I

Sieving Coefficients for a conventional high-flux
dialysis membrane, Polyflux ® 170H (Gambro Lundia AB), and a
High Cut-Off dialysis membrane, HCO 1100 ®(Gambro Lundia
AB). The Sieving Coefficients in plasma have been determined
according to DIN EN1283 (maximum blood flow, 20% of
blood flow UF. HCO1100: QB = 400 mL/min; UF = 80 mL/min. P170H:
QB = 500 mL/min; UF = 100 mL/min. For the Sieving Coefficients
in aqueous solution the following flow rates were used:
HCO1100: QB = 228 mL/min, UF = 46 mL/min. P170H:
QB = 234 mL/min, UF = 67 mL/min.
Sieving coefficients (%)

| | Filter type | |
|---|---|---|
| | Plasma Validation | Aqueous Validation/Others |
| P170H | | |
| Vitamin B12 | 100 | n.d. |
| Inulin | 100 | n.d. |
| beta2M | 75 | n.d. |
| Myoglobin | 25 | 70 |
| Albumin | <1 | 8 |
| HCO 1100 | | |
| Vitamin B12 | 100 | n.d. |
| Inulin | 100 | n.d. |
| beta2M | n.d. | n.d. |
| Myoglobin | 95 | 97-98 |
| Albumin | 10 | 46-53 |

More preferably, the membrane is a permselective membrane of the type disclosed in WO 2004/056460. Such membranes preferably allow passage of molecules having a molecular weight of up to 45 kDa in the presence of whole blood and have a molecular weight exclusion limit in water of about 200 kDa. In one embodiment of the invention, the membrane takes the form of a permselective asymmetric hollow fiber membrane. It preferably comprises at least one hydrophobic polymer and at least one hydrophilic polymer. Preferably the polymers are present as domains on the surface.

In one embodiment, the membrane is free light chain (FLC) leaking. That is, the κ or λ free light chains pass through the membrane. High flux membranes, with smaller pore sizes, have been observed to remove some free light chains. However, this appears to be primarily due to binding of the FLC onto the dialysis membranes. FLC may be used as markers of middle molecular weight proteins. Although clearing of free light chains is not a primary target of the invention, their reduction can be used as an indicator of membrane functionality.

According to one aspect of the invention, a High Cut-off dialysis membrane that allows the passage of molecules having a molecular weight of up to 45 kDa with a sieving coefficient of 0.1 to 1.0 in the presence of whole blood, and with a molecular weight exclusion limit in water of 200 kDa is provided for treating conditions of liver failure. The treatment preferably consists in the elimination of protein-bound toxins from the patient's blood wherein the dialysate contains human serum albumin (HSA).

Preferably, the treatment is directed to removing albumin bound toxins and inflammatory mediators, especially cytokines, from the blood of patients suffering from liver failure.

The treatment preferably results in a reduced blood level of protein-bound toxins and inflammatory mediators.

According to another aspect of the invention, a liver dialysis device, especially to support the liver function during conditions of liver failure, is provided, which device comprises a dialysis membrane, in the blood circuit, that allows the passage of molecules having a molecular weight of up to 45 kDa with a sieving coefficient of 0.1 to 1.0 in the presence of whole blood, and with a molecular weight exclusion limit in water of about 200 kDa. It is provided, in a further aspect of the invention, a liver dialysis system wherein the dialysis membrane has a sieving coefficient for albumin, in plasma, of from 0.1 to 0.2 and a sieving coefficient for myoglobin, in plasma, of from 0.85 to 1.0.

It is provided, in a further aspect of the invention, a liver dialysis system wherein the dialysis membrane has a clearance (ml/min) for κ-FLC of from 35 to 40, and for λ-FLC of from 30 to 35. Clearance is determined in vitro (±20%) with $Q_B$=250 ml/min, $Q_D$=500 ml/min, $U_F$=0 ml/min in bovine plasma having a protein level of 60 g/l at 37° C. The plasma level is for human κ=500 mg/l and human λ=250 mg/l.

According to yet another aspect of the invention, a liver device especially to support the liver function during conditions of liver failure, is provided, which device comprises a dialysis membrane, in the blood circuit, that allows the passage of molecules having a molecular weight of up to 45 kDa with a sieving coefficient of 0.1 to 1.0 in the presence of whole blood, and with a molecular weight exclusion limit in water of about 200 kDa, wherein the dialysate comprises HSA in the range of from 1% by weight to 25% by weight. Preferably, HSA concentration lies in the range of from 2% by weight to 20% by weight.

Preferably, a dialysis membrane of the invention comprises at least one hydrophilic polymer and at least one hydrophobic polymer. In one embodiment, at least one hydrophilic polymer and at least one hydrophobic polymer are present in the dialysis membrane as domains on the surface of the dialysis membrane.

The hydrophobic polymer may be chosen from the group consisting of polyarylethersulfone (PAES), polypropylene (PP), polysulfone (PSU), polymethylmethacrylate (PMMA), polycarbonate (PC), polyacrylonitrile (PAN), polyamide (PA), or polytetrafluoroethylene (PTFE).

The hydrophilic polymer may be chosen from the group consisting of polyvinylpyrrolidone (PVP), polyethyleneglycol (PEG), polyvinylalcohol (PVA), and copolymer of polypropyl-eneoxide and polyethyleneoxide (PPO-PEO).

In one embodiment, the dialysis membrane is a hollow fiber having at least a 3-layer asymmetric structure with a separation layer present in the innermost layer of the hollow fiber. Preferably the separation layer has a thickness of lees than 0.5 μm. Preferably, the separation layer contains pore channels having a pore size of 15 to 60 nm, more preferably 20 to 40 nm.

The next layer in the hollow fiber membrane is the second layer, having the form of a sponge structure and serving as a support for said first layer. In a preferred embodiment, the second layer has a thickness of about 1 to 15 μm.

The third layer has the form of a finger structure. Like a framework, it provides mechanical stability on the one hand; on the other hand a very low resistance to the transport of molecules through the membrane, due to the high volume of voids. During the transport process, the voids are filled with water and the water gives a lower resistance against diffusion and convection than a matrix with a sponge-filled structure having a lower void volume. Accordingly, the third layer provides mechanical stability to the membrane and, in a preferred embodiment, has a thickness of 20 to 60 μm.

In one embodiment, the membrane also includes a fourth layer, which is the outer surface of the hollow fiber membrane. In this preferred embodiment, the outer surface has openings of pores in the range of 0.5 to 3 μm and the number of said pores is in the range of from 10,000 to 150,000 pores/mm², preferably 20000 to 100000 pores/mm². This fourth layer preferably has a thickness of 1 to 10 μm.

The manufacturing of the membrane of the present invention follows a phase inversion process, wherein a polymer or a mixture of polymers is dissolved in a solvent to form a polymer solution. The solution is degassed and filtered and is thereafter kept at an elevated temperature.

Subsequently, the polymer solution is extruded through a spinning nozzle (for hollow fibers) or a slit nozzle (for a flat film) into a fluid bath containing a non-solvent for the polymer. The non-solvent replaces the solvent and thus the polymer is precipitated to an inverted solid phase.

To prepare a hollow fiber membrane, the polymer solution preferably is extruded through an outer ring slit of a nozzle having two concentric openings. Simultaneously, a center fluid is extruded through an inner opening of the nozzle. At the outlet of the spinning nozzle, the center fluid comes in contact with the polymer solution and at this time the precipitation is initialized. The precipitation process is an exchange of the solvent from the polymer solution with the non-solvent of the center fluid.

By means of this exchange the polymer solution inverses its phase from the fluid into a solid phase. In the solid phase the pore structure, i.e. asymmetry and the pore size distribution, is generated by the kinetics of the solvent/non-solvent exchange. The process works at a certain temperature which influences the viscosity of the polymer solution. The temperature at the spinning nozzle and the temperature of the polymer solution and center fluid is 30 to 80° C. The viscosity determines the kinetics of the pore-forming process through the exchange of solvent with non-solvent. Subsequently, the membrane is preferably washed and dried.

By the selection of precipitation conditions, e.g. temperature and speed, the hydrophobic and hydrophilic polymers are "frozen" in such a way that a certain amount of hydrophilic end groups are located at the surface of the pores and create hydrophilic domains. The hydrophobic polymer builds other domains. A certain amount of hydrophilic domains at the pore surface area are needed to avoid adsorption of proteins. The size of the hydrophilic domains should preferably be within the range of 20 to 50 nm. In order to repel albumin from the membrane surface, the hydrophilic domains also need to be within a certain distance from each other. By the repulsion of albumin from the membrane surface, direct contact of albumin with the hydrophobic polymer, and consequently the adsorption of albumin, are avoided.

The polymer solution used for preparing the membrane preferably comprises 10 to 20 wt.-% of hydrophobic polymer and 2 to 11 wt.-% of hydrophilic polymer. The center fluid generally comprises 45 to 60 wt.-% of precipitation medium, chosen from water, glycerol and other alcohols, and 40 to 55 wt.-% of solvent. In other words, the center fluid does not comprise any hydrophilic polymer.

In a preferred embodiment, the polymer solution coming out through the outer slit openings is, on the outside of the precipitating fiber, exposed to a humid steam/air mixture. Preferably, the humid steam/air mixture has a temperature of at least 15° C., more preferably at least 30° C., and not more than 75° C., more preferably not more than 60° C.

Preferably, the relative humidity in the humid steam/air mixture is between 60 and 100%. Furthermore, the humid steam in the outer atmosphere surrounding the polymer solution emerging through the outer slit openings preferably includes a solvent. The solvent content in the humid steam/air mixture is preferably between 0.5 and 5 wt.-%, related to the water content. The effect of the solvent in the temperature-controlled steam atmosphere is to control the speed of precipitation of the fibers. When less solvent is employed, the outer surface will obtain a denser surface, and when more solvent is used, the outer surface will have a more open structure. By controlling the amount of solvent within the temperature-controlled steam atmosphere surrounding the precipitating membrane, the amount and size of the pores on the outer surface of the membrane are controlled, i.e. the size of the openings of the pores is in the range of from 0.5 to 3 μm and the number of said pores is in the range of from 10,000 to 150,000 pores/mm², preferably 20,000 to 100,000 pores/mm². The fourth layer of the membrane is preferably prepared by this method.

Before the extrusion, suitable additives may be added to the polymer solution. The additives are used to form a proper pore structure and optimize the membrane permeability, the hydraulic and diffusive permeability, and the sieving properties. In a preferred embodiment, the polymer solution contains 0.5 to 7.5 wt.-% of a suitable additive, preferably chosen from the group comprising water, glycerol and other alcohols.

The solvent may be chosen from the group comprising n-methylpyrrolidone (NMP), dimethyl acetamide (DMAC), dimethyl sulfoxide (DMSO) dimethyl formamide (DMF), butyrolactone and mixtures of said solvents.

In one embodiment of the invention, the sieving coefficient of the High Cut-off dialysis membrane for IL-6 in the presence of whole blood is 0.9 to 1.0 and the sieving coefficient for albumin in the presence of whole blood is less than 0.1. In yet another embodiment, said sieving coefficient for albumin is less than 0.05.

As used herein, the term "sieving coefficient (S)" refers to the physical property of a membrane to exclude or pass molecules of a specific molecular weight. The sieving coefficient can be determined according to standard EN 1283, 1996.

Put simply, the sieving coefficient of a membrane is determined by pumping a protein solution (bovine or human plasma) under defined conditions (QB, TMP and filtration rate) through a membrane bundle and determining the concentration of the protein in the feed, in the retentate and in the filtrate. If the concentration of the protein in the filtrate is zero, a sieving coefficient of 0% is obtained. If the concentration of the protein in the filtrate equals the concentration of the protein in the feed and the retentate, a sieving coefficient of 100% is obtained.

The sieving coefficient, S, is calculated according to $S=(2C_F)/(C_{Bin}+C_{Bout})$, where $C_F$ is the concentration of a solute in the filtrate; $C_{Bin}$ is the concentration of a solute at the blood inlet side of the device under test; and $C_{Bout}$ is the concentration of a solute at the blood outlet side of the device under test.

Furthermore, the sieving coefficient allows determining the nominal cut-off of a membrane (corresponding to a sieving coefficient of 0.1). As used herein the term "cut-off" refers to the molecular weight of a substance having a sieving coefficient (S) of 0.1.

The membrane of the present invention allows the passage of molecules having molecular weights up to 45 kDa in the presence of whole blood/blood proteins, which means that it has a sieving coefficient (S) of 0.1 to 1.0 in presence of whole blood for substances having a molecular weight of less than 45 kDa.

Methods for producing suitable membranes are disclosed, for example, in WO 2004/056460, incorporated herein by reference. An example of a suitable membrane is available from Gambro under the trade name "HCO 1100®". The HCO 1100® dialyzer comprises a steam sterilized membrane based on polyethersulfone and polyvinylpyrrolidone with a wall thickness of 50 μm and an inner diameter of 215 μm. The in vivo albumin loss (HD) of the HCO 1100® at $Q_D$=500 ml/min is 1.5 g per hour of dialysis.

If no other meaning for this expression is indicated, the term "High Cut-off membrane" or "High Cut-off dialysis membrane" as used herein is used to describe a membrane according to the invention, i.e. a membrane which allows passage of molecules having a molecular weight of up to 45 kDa with a sieving coefficient of 0.1 to 1.0 in the presence of whole blood. Specific embodiments of such High Cut-off dialysis membranes in addition may have a molecular weight exclusion limit in water of about 200 kDa with a sieving coefficient of 0.1 to 1.0 The sieving coefficient in water-can be determined according to Leypoldt et al., *Trans Am Soc Artif Intern Organs*. 1983; 29:678-83. The membrane is otherwise characterized by sieving coefficients as indicated in FIG. 2.

The term "liver failure" in the context of the present invention refers to the inability of the liver to perform its normal synthetic and metabolic function as part of normal physiology. Liver failure thus leads to an insufficient detoxification of albumin, which is followed by an exhaustion of the binding capacity of the albumin and an enrichment of the otherwise albumin-bound toxins, e.g. of unconjugated bilirubin. Treatment is indicated, for example, at a bilirubin concentration of >10 mg/dL. However, there are liver disorders where a liver dialysis treatment is indicated, but which is not characterized by increased bilirubin levels. Disorders which are associated with the expression "liver failure" as used in the present invention include, but are not limited to, hepatorenal syndrome, decompensated chronic liver disease, acute liver failure, graft dysfunction after liver transplantation, liver failure after liver surgery, secondary liver failure, multi organ failure or intractable pruritus in cholestasis.

It will be readily apparent to one skilled in the art that various substitutions and modifications may be made to the invention disclosed herein without departing from the scope and spirit of the invention.

The present invention will now be illustrated by way of non-limiting examples of preferred embodiments in order to further facilitate the understanding of the invention.

EXAMPLES

Example 1

HSA Concentration in the System

It was the goal of the present experiment to monitor the development of the HSA concentration within the liver support system. The development of the HSA concentration is of interest, as the High Cut-off dialysis membrane allows, to a certain extent, the passage of albumin (see also Table 1). For this test a standard MARS system with an AK95/MARS Monitor were used, in combination with a 2.1 m² High Cut-off dialysis membrane, hereinafter referred to as P5SH (FIG. 1 (3)). The P5SH dialyzer is equivalent to the HCO 1100® dialyzer, with the exception of the membrane area which is smaller in the HCO 1100® version. The P5SH filter was used to have a membrane area which is equivalent to the conventional MARSFlux® filter membrane area. Further, a diaFlux 1.4 filter (FIG. 1 (4)) was used. The activated carbon adsorber was AC 250 AE, the anion exchanger was IE 250. Unconjugated bilirubin was from Sigma (EC 211-239-7). Bile acid (chenodeoxycholic acid) was from Sigma (Lot 094K075). 20% human serum albumin was from Baxter (Lot VNA1F007). The plasma (FIG. 1 (1)) used was Octaplas® SD virally inactivated human plasma from Octapharma (Lot 548 209 950). The blood circuit (re-circulating) of the test system contained 3 l plasma, unconjugated bilirubin (100 mg/l) and chenodesoxycholic acid (100 mg/l). The albumin concentration was set to be 35 g/l. The temperature was adjusted to 37° C. The albumin circuit contained 5% or 10% human serum albumin in 0.9% NaCl solution, respectively. The dialysate circuit comprised dialysis concentrate only (138 mmol Na⁺; 1.0 mmol K⁺; 0.25 mmol Mg⁺⁺; 1.25 mmol Ca⁺⁺; 107 mmol Cl⁻; 3.0 mmol acetat; 32.0 mmol $HCO^{3-}$) and a BiCart® cartridge containing sodium bicarbonate. Test samples for albumin analysis were taken at $B_{in}$ and $Alb_1$. Test samples for the analysis of unconjugated bilirubin and chenodesoxycholic acid were taken at $B_{in}$, $B_{out}$, $Alb_1$, $Alb_{1.1}$, $Alb_2$ and $Alb_3$ after 0, 10, 20, 30, 40, 60, 80, 100, 120, 180, 240, 300 and 360 minutes. Treatment parameters in the test were $Q_B$: 175 ml/min; $Q_{Alb}$: 175 ml/min; $Q_D$: 500 ml/min; UF: 0 ml/min. Treatment time was 6 hours. Analysis of clearance rates for bile acids, diazepam, ammonium and creatinin is done according to the following formula:

$$K = \ln\frac{C_0}{C_t} * \frac{V_{Pool}}{t}$$

For determining the clearance rates for bilirubin, the following formula is used:

$$K = \frac{(C_0 - C_t) * V_{Pool}}{t * C_0}$$

Additionally, the reduction rate is determined according to the following formula:

$$RR = cBin_{0\ min}[\%] - cBin_{360\ min}[\%].$$

Figure 3:
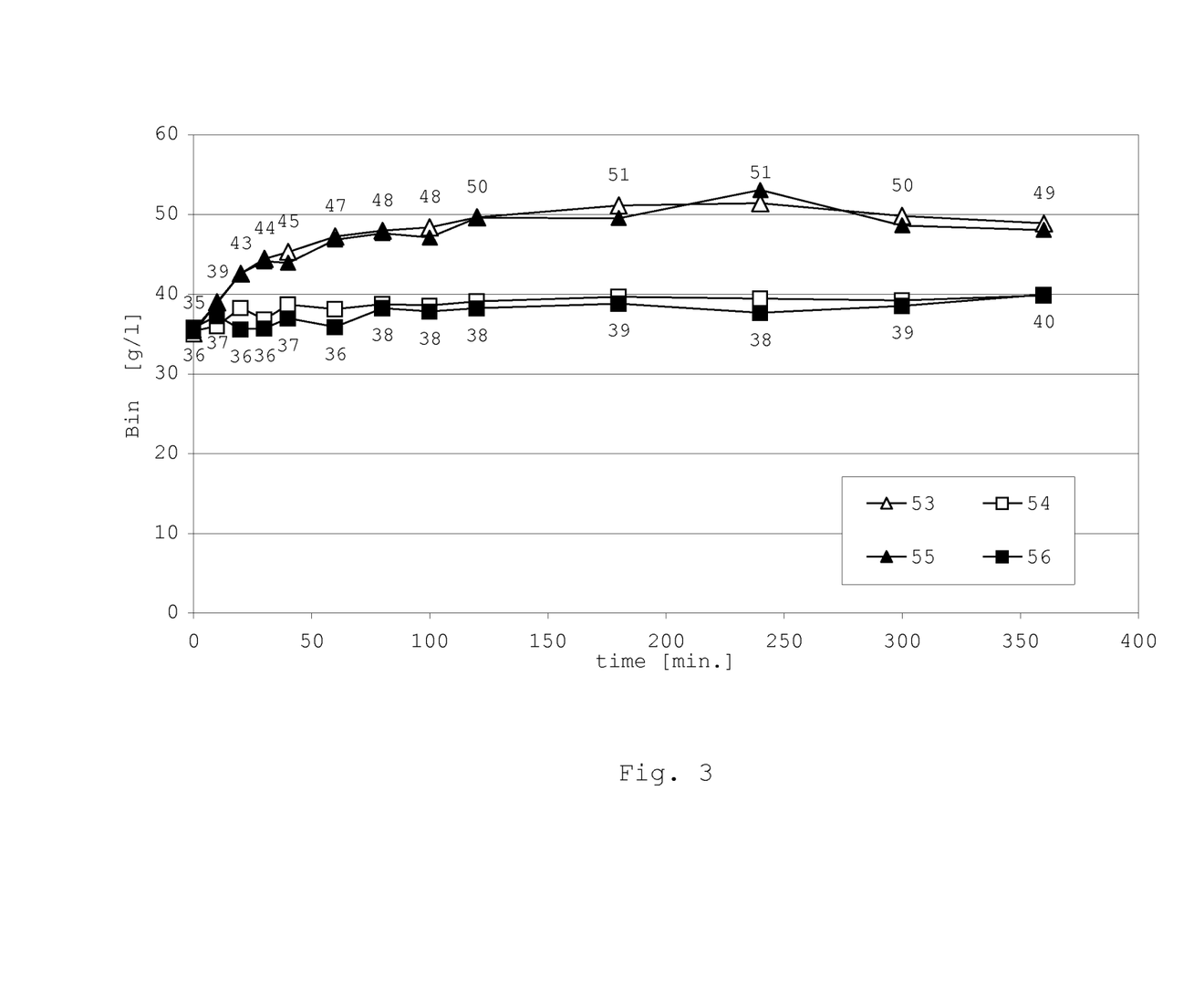
FIG. 3 shows the development of the HSA concentration within the blood circuit as determined at $B_{in}$ during the testing. Tests 54 and 56 were run with a HSA concentration of 5% (50 g/l). Tests 53 and 55 were run with a HSA concentration of 10% (100 g/l).

FIG. 3 shows the development of the HSA concentration as determined at $B_{in}$ during the testing, i.e. within the blood circuit. Tests 54 and 56 were run with a HSA concentration of 5% (50 g/l). Tests 53 and 55 were run with a HSA concentration of 10% (100 g/l).

As can be seen, albumin can pass the membrane of the HCO 1100® dialyzer. Therefore, the concentration of albumin in the blood circuit, which was 35 g/l at the beginning, slowly increases over time as the albumin concentration in the albumin and blood circuit move in the direction of equilibrium. The HSA concentration of the blood circuit finally reaches 40 and 49 g/l, respectively.

Figure 4:
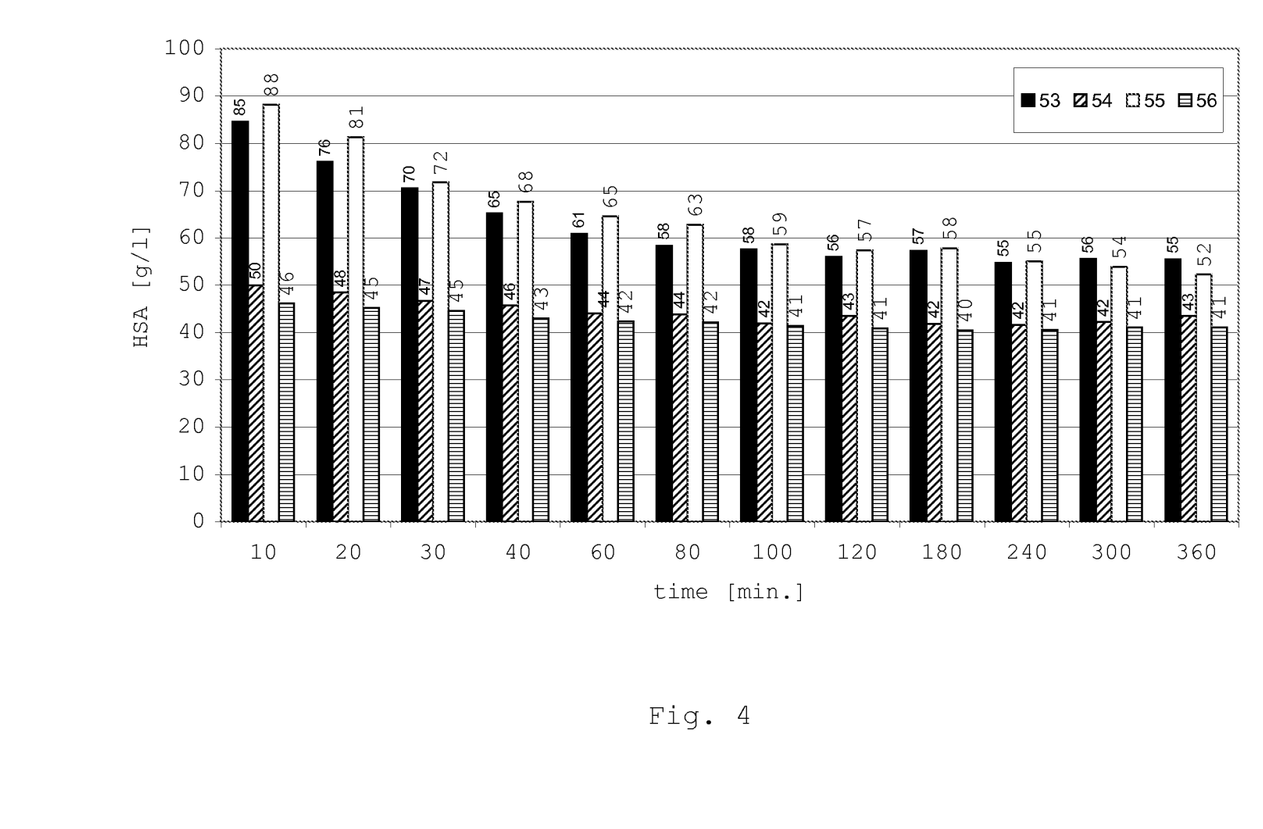
FIG. 4 shows the development of the HSA concentration in the albumin circuit. Tests 54 and 56 were run with a HSA concentration of 5% (50 g/l). Tests 53 and 55 were run with a HSA concentration of 10% (100 g/l).

FIG. 4 shows the development of the HSA concentration in the albumin circuit in the same tests 53, 54, 55 and 56. As expected with regard to the blood circuit results, the albumin concentration in the albumin circuit which started from 50 g/l or 100 g/l, respectively, decreases as albumin passes the membrane of the dialyzer (3) into the blood circuit where the concentration is lower. After 360 minutes the albumin concentration reaches 41 g/l and 52 g/l, respectively. Tests 53 and 55 (100 g/l albumin in the albumin circuit) result in an albumin concentration of 49 g/l in the blood circuit and 54 g/l in the albumin circuit after 6 h. Tests 54 and 56 (50 g/l albumin in the albumin circuit) result in an albumin concentration of 40 g/l in the blood circuit and 42 g/l in the albumin circuit after 6 h.

Example 2

Bilirubin Reduction

Figure 5A:
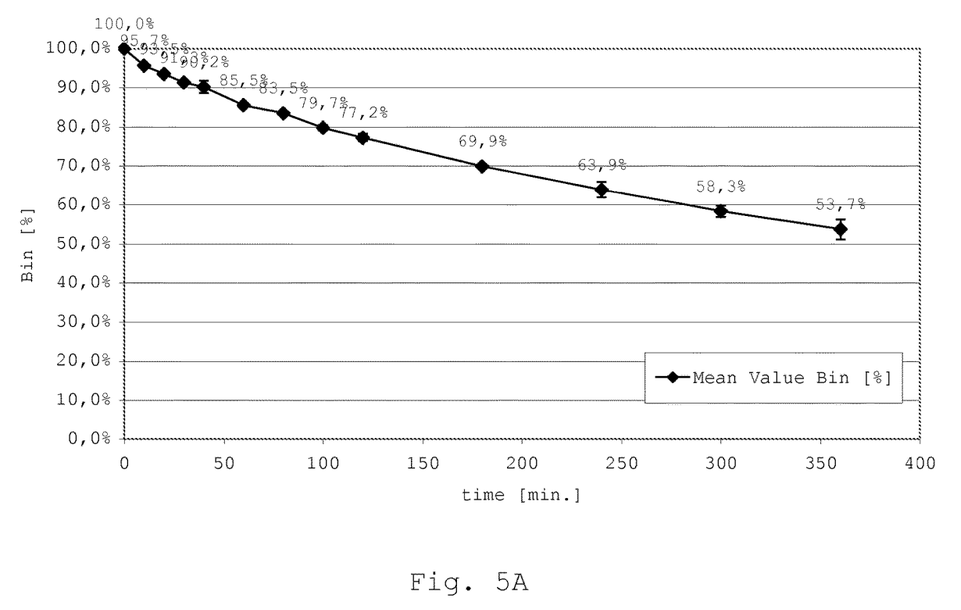
Figure 5B:
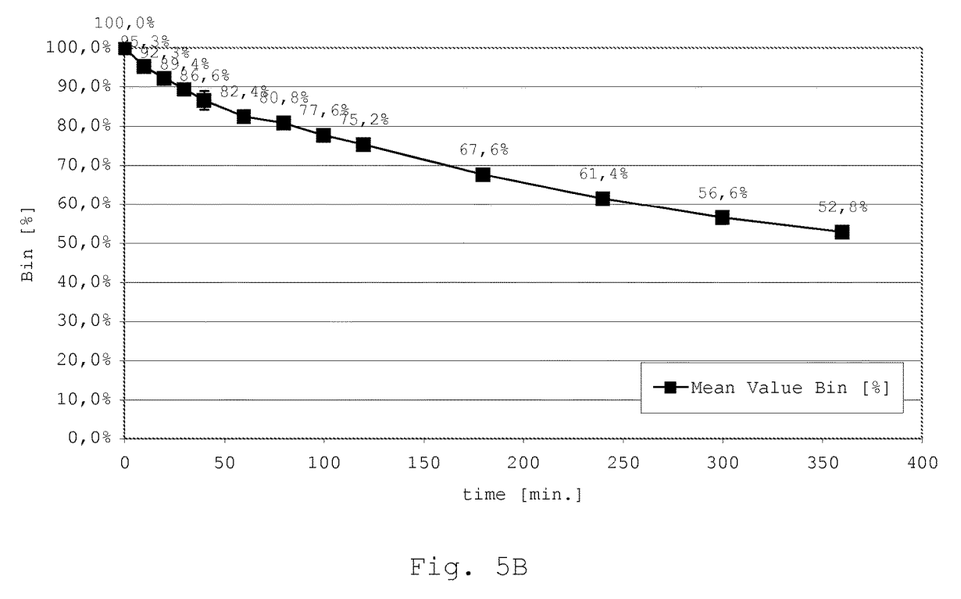

Tests were done as described in Example 1. The albumin concentration was again 5% and 10%. The concentration of unconjugated bilirubin was determined in samples taken at $B_{in}$. FIG. 5 A depicts the development of the bilirubin concentration in the blood circuit when the HSA concentration in the albumin circuit is 10% at 0 min. FIG. 5 B depicts the development of the bilirubin concentration in the blood circuit when the HSA concentration in the albumin circuit is 5% at 0 min. As can be seen, the bilirubin concentration decreases in both system settings. The reduction rate is about 47% in both cases.

Example 3

Bile Acid Reduction

Figure 6A:
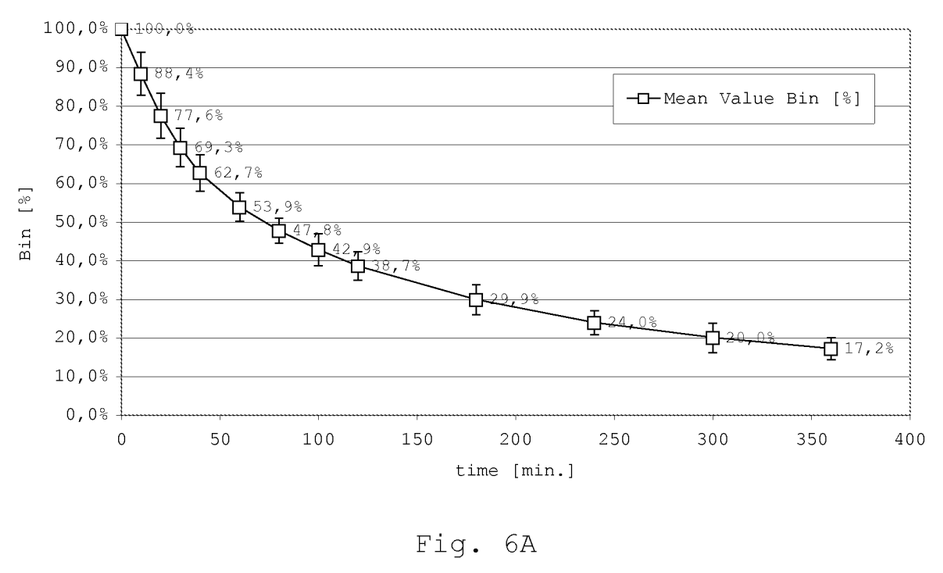
Figure 6B:
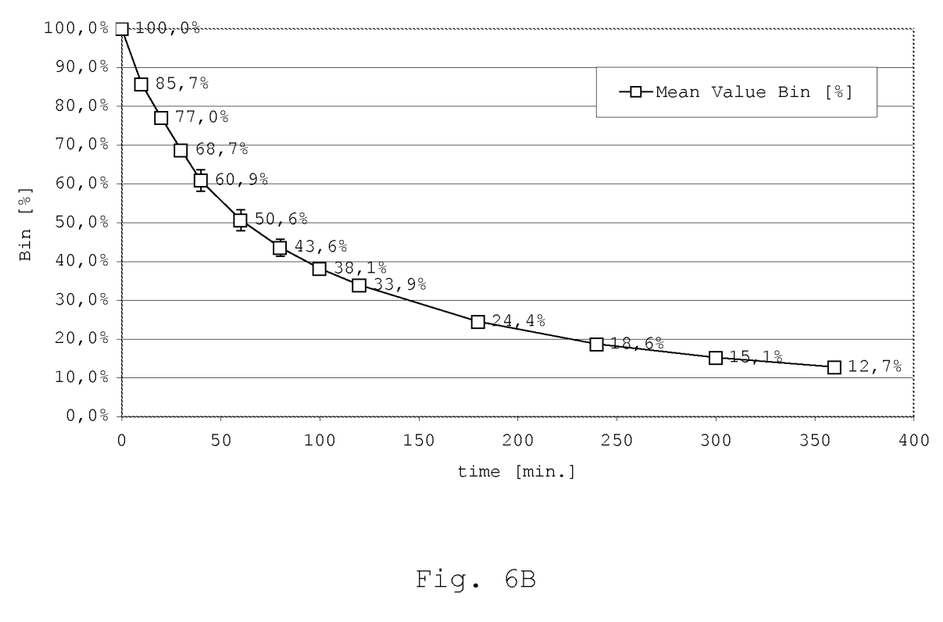

Tests were done as described in Example 1. The albumin concentration was again 5% and 10%. The concentration of bile acid was determined in samples taken at $B_{in}$. FIG. 6 A depicts the development of the bile acid concentration in the blood circuit when the HSA concentration in the albumin circuit is 10% at 0 min. FIG. 6 B depicts the development of the bile acid concentration in the blood circuit when the HSA concentration in the albumin circuit is 5% at 0 min. As can be seen, the bile acid concentration decreases in both system settings. The reduction rate is about 83% at a HSA concentration of 10% and 87% at a HSA concentration of 5%.

Example 4

Comparison Between Conventional High-Flux and High Cut-Off Dialysis Membrane: Removal of Unconjugated Bilirubin and of Bile Acids Tests were performed as described in Example 1 to 3. However, a conventional MarsFlux 2.1 filter was used instead of the P5SH dialyzer. The results were compared with the results obtained with the P5SH dialyzer according to the above Examples.

Figure 7:
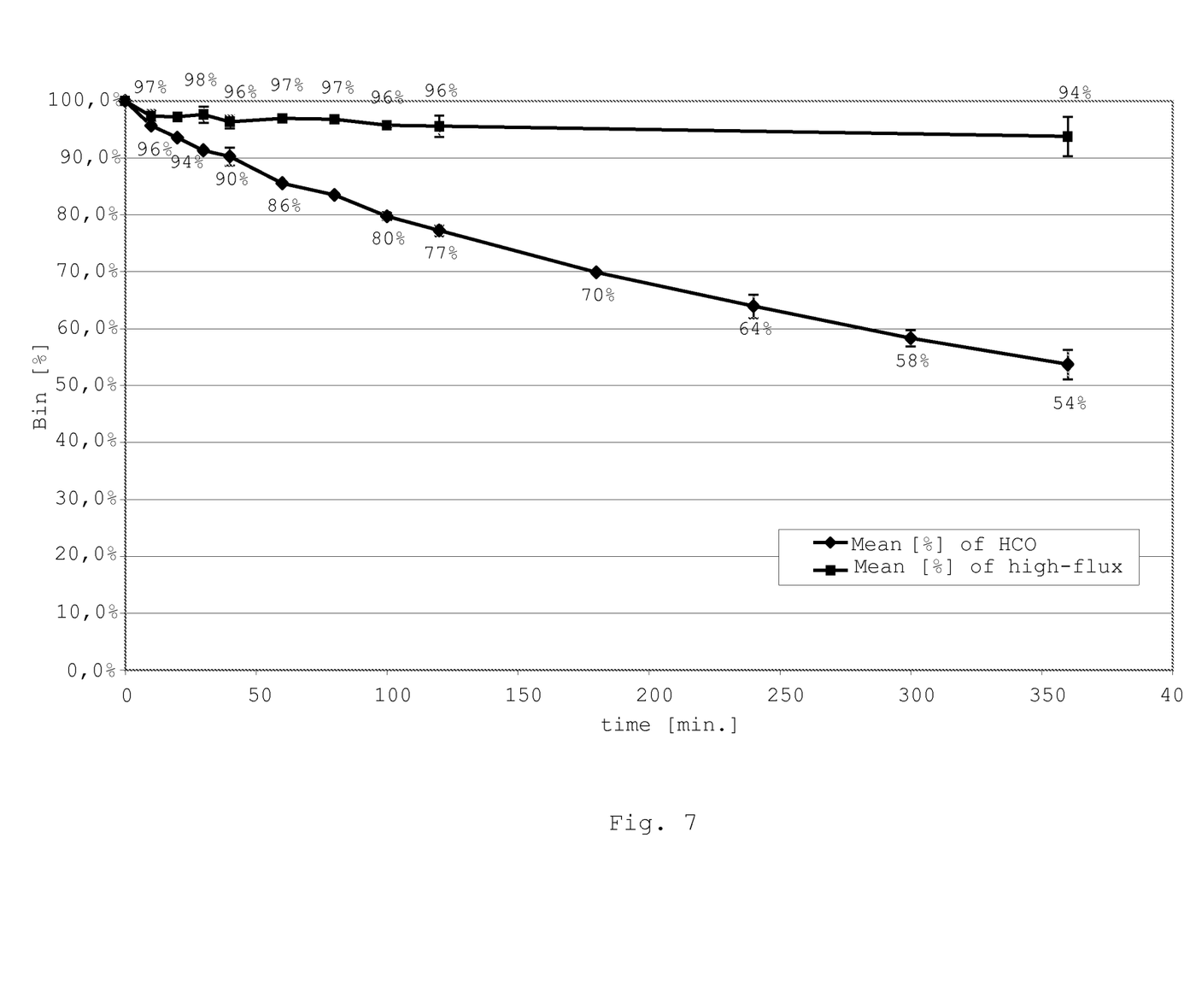
FIG. 7 depicts the development of the concentration of unconjugated bilirubin in the blood circuit in a liver dialysis system using a High Cut-off (HCO) membrane (P5SH) according to the invention and in a liver dialysis system using a conventional MARS®Flux high-flux filter. Samples were obtained from the blood circuit, $B_{in}$.

FIG. 7 depicts the development of the concentration of unconjugated bilirubin over 360 minutes in a liver dialysis system using the P5SH dialyzer and in a liver dialysis system using a conventional MARSFlux filter. Samples were taken from the blood circuit, $B_{in}$. Two tests which were run with the MARSFlux filter resulted in a reduction of unconjugated bilirubin of 6%. Two analogous tests with the P5SH dialyzer resulted in a seven-fold better reduction rate of 46%.

Figure 8:
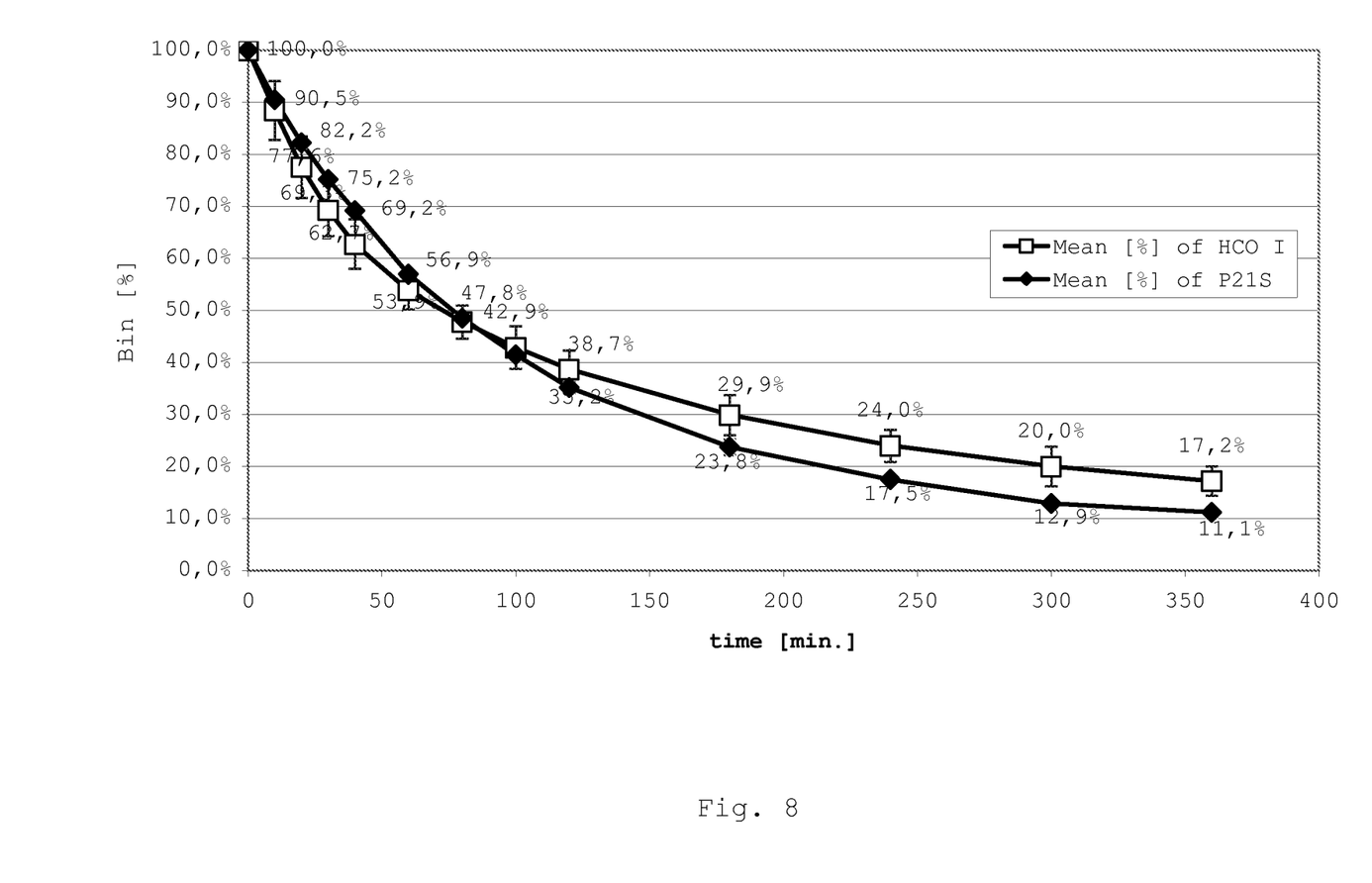
FIG. 8 shows the development of the concentration of bile acid in the blood circuit over 6 hours in a liver dialysis system using a High Cut-off membrane (P5SH) and in a liver dialysis system using a conventional MARS®Flux high-flux filter. Samples were taken at $B_{in}$.

FIG. 8 shows the development of the concentration of bile acid in the blood circuit over 6 hours in a liver dialysis system using the P5SH dialyzer and in a liver dialysis system using a conventional MARSFlux filter. Samples were taken at $B_{in}$. Two tests were run with each of the filters. Results show that the MARSFlux filter achieves a reduction rate for bile acids of 87%. The P5SH dialyzer achieves a reduction rate of 83%, which means that there is no improvement with regard to the removal of bile acids. However, the reduction rate is not worse than what can be achieved with the conventional filter. During the first 80 minutes of the treatment the P5SH dialyzer shows a better efficiency regarding the removal of bile acids. However, after 80 minutes the MARSFlux filter shows a somewhat better removal rate.

The invention claimed is:

1. A method for treatment of liver failure, the method comprising:
    passing blood of a patient with liver failure into a dialysis device comprising a dialysis membrane that allows the passage of molecules having a molecular weight of up to 45 kDa with a sieving coefficient of about 0.1 to about 1.0 in the presence of whole blood, wherein the dialysis membrane has a sieving coefficient in plasma for albumin of from about 0.1 to about 0.2, and wherein the dialysis membrane has a sieving coefficient in plasma for myoglobin of from about 0.85 to about 1.0, wherein the dialysis device comprises a dialysis side and a dialysate side, and
    wherein dialysate on the dialysis side of the dialysis device is an albumin solution comprising human serum albumin at a concentration of from about 5% to about 12% by weight;
    recycling the albumin solution by passing it through a low-flux dialyzer opposite of an aqueous buffered solution for the removal of water-soluble substances from the albumin solution;
    passing the recycled albumin solution into the dialysate side of the dialysis device; and
    returning the blood from the dialysis device to the patient.

2. The method for treatment of claim 1, wherein the method reduces concentration of protein-bound toxins and inflammatory cytokines in blood of the patient.

3. The method for treatment of claim 1, wherein the method reduces concentration of unconjugated bilirubin and bile acids in blood of the patient.

4. The method for treatment of claim 3, wherein the reduction in concentration of unconjugated bilirubin is a reduction of about 47% after 6 hours of treatment.

5. The method for treatment of claim 3, wherein the reduction in concentration of unconjugated bilirubin is about a 40% improvement in reduction of unconjugated bilirubin compared to a dialysis device comprising a high flux dialysis membrane.

6. The method for treatment of claim 1, wherein at least one hydrophilic polymer and at least one hydrophobic polymer are present as domains on the surface of the dialysis membrane.

7. The method for treatment of claim 1, wherein the dialysis membrane is a hollow fiber membrane and has at least a 3-layer asymmetric structure, wherein the at least 3-layer asymmetric structure comprises an innermost layer, and wherein the innermost layer comprises a separation.

8. The method for treatment of claim 7, wherein the dialysis membrane has pores in the separation layer, said pores having a diameter in the range of about 15 to about 60 nm.

9. The method for treatment of claim 7, wherein the dialysis membrane has pores in the separation layer, said pores having a diameter in the range of about 20 to about 40 nm.

10. The method for treatment of claim 1, wherein the step of recycling the albumin solution further comprises passing it through an activated carbon adsorber, a filter for removing carbon particles, and an anion exchanger.

11. The method for treatment of claim 1, wherein dialysate on the dialysis side of the dialysis device is an albumin solution comprising human serum albumin at a concentration of about 5% by weight.

12. The method for treatment of claim 1, wherein dialysate on the dialysis side of the dialysis device is an albumin solution comprising human serum albumin at a concentration of about 10% by weight.

* * * * *